United States Patent
Plos et al.

(10) Patent No.: US 11,090,252 B2
(45) Date of Patent: Aug. 17, 2021

(54) PROCESS FOR STRAIGHTENING KERATIN FIBRES WITH A COMPOSITION COMPRISING A UREA AND/OR A UREA DERIVATIVE AND A POLYMERIC THICKENER

(71) Applicant: L'OREAL, Paris (FR)

(72) Inventors: Grégory Plos, Paris (FR); Patrice Lerda, Asnieres (FR); Anne Bouchara, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/230,323

(22) Filed: Dec. 21, 2018

(65) Prior Publication Data

US 2019/0117551 A1 Apr. 25, 2019

Related U.S. Application Data

(62) Division of application No. 14/786,608, filed as application No. PCT/EP2014/058453 on Apr. 25, 2014, now abandoned.

(30) Foreign Application Priority Data

Apr. 25, 2013 (FR) ....................... 1353774
Apr. 25, 2013 (FR) ....................... 1353775

(51) Int. Cl.
| | |
|---|---|
| A61Q 5/04 | (2006.01) |
| A61K 8/87 | (2006.01) |
| A61K 8/86 | (2006.01) |
| A45D 7/06 | (2006.01) |
| A45D 2/00 | (2006.01) |
| A61K 8/42 | (2006.01) |
| A61K 8/73 | (2006.01) |
| A61K 8/81 | (2006.01) |
| A61Q 5/12 | (2006.01) |

(52) U.S. Cl.
CPC ............. *A61K 8/87* (2013.01); *A45D 2/001* (2013.01); *A45D 7/06* (2013.01); *A61K 8/42* (2013.01); *A61K 8/731* (2013.01); *A61K 8/8152* (2013.01); *A61K 8/86* (2013.01); *A61K 2800/48* (2013.01); *A61K 2800/49* (2013.01); *A61K 2800/548* (2013.01); *A61K 2800/5424* (2013.01); *A61K 2800/592* (2013.01); *A61Q 5/04* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 3,915,921 A | 10/1975 | Schlatzer, Jr. | |
| 4,137,180 A | 1/1979 | Naik et al. | |
| 4,228,810 A | 10/1980 | Moore et al. | |
| 4,509,949 A | 4/1985 | Huang et al. | |
| 4,874,554 A | 10/1989 | Lange et al. | |
| 5,051,252 A | 9/1991 | Schultz et al. | |
| 5,089,578 A | 2/1992 | Valint et al. | |
| 6,010,707 A | 1/2000 | Philippe et al. | |
| 6,429,231 B1 | 8/2002 | Bhagwat et al. | |
| 6,822,039 B1 | 11/2004 | Monfreux-Gaillard et al. | |
| 8,192,729 B2 | 6/2012 | Saute et al. | |
| 8,343,238 B1 | 1/2013 | Lopez et al. | |
| 2003/0124079 A1 | 7/2003 | Mougin et al. | |
| 2004/0141943 A1 | 7/2004 | Mougin et al. | |
| 2007/0009461 A1 | 1/2007 | Chandra et al. | |
| 2009/0071493 A1 | 3/2009 | Nguyen et al. | |
| 2009/0247650 A1 | 10/2009 | Mougin et al. | |
| 2010/0311627 A1* | 12/2010 | Hloucha | A61K 8/068 510/121 |
| 2011/0052520 A1* | 3/2011 | Nguyen | A61K 8/41 424/70.4 |
| 2011/0256084 A1* | 10/2011 | Dixon | A61K 8/042 424/70.2 |
| 2011/0308541 A1* | 12/2011 | Chia | A61Q 5/12 132/207 |
| 2013/0164248 A1 | 6/2013 | Khenniche | |
| 2013/0289080 A1 | 10/2013 | Masse et al. | |

FOREIGN PATENT DOCUMENTS

| | | |
|---|---|---|
| EP | 0750899 A2 | 1/1997 |
| EP | 1889602 A2 | 2/2008 |
| EP | 2275078 A2 | 1/2011 |

(Continued)

OTHER PUBLICATIONS

International Search Report for PCT/EP2014/058453, dated Jan. 29, 2015.
Porter, M.R., "Handbook of Surfactants," published by Blackie & Son (Glasgow and London), 1991, pp. 116-178.
Morishima, Yotaro, "Self-Assembling Amphiphilic Polyelectrolytes and their Nanostructures," Chinese Journal of Polymer Science, vol. 18, No. 40, (2000), pp. 323-336.

(Continued)

*Primary Examiner* — Jyothsna A Venkat

(74) *Attorney, Agent, or Firm* — The Marbury Law Group, PLLC

(57) ABSTRACT

The invention relates to a cosmetic composition comprising: (a) at least 2% by weight, relative to the total weight of the composition, of one or more compounds chosen from urea and/or urea derivatives, (b) one or more polymeric thickeners chosen from nonionic, cationic, amphoteric polymeric associative thickeners or anionic polymeric associative thickeners comprising one or more acrylic and/or methacrylic units. The invention also relates to the use of this composition for straightening keratin fibres. Finally the invention relates to a process for straightening keratin fibres.

11 Claims, No Drawings

(56) References Cited

FOREIGN PATENT DOCUMENTS

| | | |
|---|---|---|
| EP | 2387987 A1 | 11/2011 |
| FR | 2811993 A1 | 1/2002 |
| WO | 98/44012 A1 | 10/1998 |
| WO | 00/31154 A1 | 6/2000 |
| WO | 00/68282 A1 | 11/2000 |

OTHER PUBLICATIONS

Noda, Tetsuya, et al., "Micelle Formation of Random Copolymers of Sodium 2-(Acrylamide)-2-Methylpropanessulphonate and a Nonionic Surfactant Macromonomer in Water as Studied by Fluorescence and Dynamic Light Scattering," Macromolecules 2000, 33, pp. 3694-3704.

Noda, tetsuya et al., "Solution Properties of Micelle Networks Formed by Nonionic Moieties Covalently Bound to a Polyelectrolyte: Salt Effects on Rheological Behavior," Langmuir 2000, 16, pp. 5324-5332.

Noda, Tetsuya, et al., "Stimuli-Responsive Amphiphilic Copolymers of Sodium 2-(Acrylamido)-2-Methylpropanesulphonale and Associative Macromonomers," Polym. Preprint, Div. Polym. Chem. 1999, 40(2), pp. 220-221.

Fonnum, G. et al., "Associative Thickeners. Part I: Synthesis, Rheology and Aggregation Behavior," Colloid Polym. Sci., 271, (1993) pp. 380-389.

\* cited by examiner

PROCESS FOR STRAIGHTENING KERATIN FIBRES WITH A COMPOSITION COMPRISING A UREA AND/OR A UREA DERIVATIVE AND A POLYMERIC THICKENER

CROSS REFERENCE TO RELATED APPLICATIONS

This is a divisional application claiming priority to U.S. application Ser. No. 14/786,608, filed Oct. 23, 2015, which is a National Stage application of PCT/EP2014/058453, filed internationally on Apr. 25, 2014, as well as French Application 1353775, filed on Apr. 25, 2013, and French Application No. 1353774, filed Apr. 25, 2013, all of which are incorporated by reference herein in their entireties.

The present invention relates to a composition for the long-lasting straightening of keratin fibres, in particular of human keratin fibres such as the hair, comprising one or more compounds chosen from urea and derivatives thereof and one or more nonionic, cationic, amphoteric or anionic associative polymeric thickeners comprising one or more acrylic and/or methacrylic units.

The present invention also relates to the use of the composition according to the invention for straightening keratin fibres, in particular human keratin fibres such as the hair.

Finally, a subject of the present invention is a process for straightening keratin fibres, in particular human keratin fibres such as the hair, comprising a step of applying the composition according to the invention to the keratin fibres, and then a step of raising the temperature of the keratin fibres, using a heating means, to a temperature ranging from 25 to 250° C.

Many people are dissatisfied with the appearance of their hair; in particular, people who have curly hair usually wish to obtain straight hair, and, conversely, people who have curl-free hair wish to have curly hair.

The first of the techniques usually used for permanently reshaping the hair consists, in a first step, in opening the —S—S— disulfide bonds of keratin (keratocystine) using a composition containing a suitable reducing agent (reduction step), and then, after having rinsed the head of hair thus treated, generally with water, in reconstituting said disulfide bonds, in a second step, by applying to the hair, which has been placed under tension beforehand (with, for example, rollers), an oxidizing composition (oxidation step, also known as the fixing step) so as finally to give the hair the desired shape. This technique thus makes it possible to straighten (relax) the hair. The new shape given to the hair by a chemical treatment such as that above is permanent and in particular withstands washing with water or with shampoos, as opposed to the simple conventional techniques of temporary straightening, such as hairsetting.

The reducing compositions that may be used for the first step of a permanent straightening operation generally contain sulfites, bisulfites, alkylphosphines or, preferably, thiols as reducing agents. Among the latter, those commonly used are cysteine and various derivatives thereof, cysteamine and derivatives thereof, thiolactic acid or thioglycolic acid, and salts thereof and also esters thereof, especially glyceryl thioglycolate.

The oxidizing compositions required for performing the fixing step are usually compositions based on aqueous hydrogen peroxide solution.

In the context of hair straightening techniques, this permanent straightening operation is generally performed on curly or voluminous hair so as to obtain more or less pronounced straightening and a reduction of the volume and apparent mass of the hair.

However, such a technique is not entirely satisfactory. This is because, although this technique proves to be very effective for modifying the shape of the hair, it still degrades the hair fibres, which is mainly due to the high contents of reducing agents used in the reducing compositions and also to the various more or less long leave-on times that may be involved in such a process.

This technique can thus induce, in the long-term, impairment of the quality of the hair, leading to a decrease in its cosmetic properties, such as its sheen, and degradation of its mechanical properties, more particularly of its mechanical strength, due to swelling of the hairs during the rinsing between the reduction step and the oxidation step, which can also be reflected by an increase in the porosity of the hairs. These drawbacks are especially observed with thioglycolic acid, which is generally used in basic medium at pH values ranging from 8.5 to 9.5.

Moreover, if the technique of permanent straightening of the hair described previously is applied to hair that has undergone prior artificial coloration, it usually leads to degradation or stripping of this artificial coloration.

Similarly, if a coloration is applied to permanent-waved hair according to the technique described previously, the colour obtained is very different from the colour normally obtained on non-permanent-waved natural hair.

It has also been observed that the use of reducing agents results in an unsatisfactory durability for the straightening of the hair, in particular for the relaxing or defrizzing of the hair.

Moreover, it has also been found that the use of these reducing agents leads to scalp discomfort (irritation, itching, etc.).

Finally, it is very common to have to deal with problems of odours, both with the reducing compositions used, and in particular those containing thiols, and with the hair reduced.

The second technique usually used for obtaining hair straightening or relaxing consists in performing an operation known as lanthionization, using a composition containing a base belonging to the hydroxide family. It leads to replacement of the disulfide bonds (—CH$_2$—S—S—CH$_2$—) with lanthionine bonds (—CH$_2$—S—CH$_2$—). This lanthionization operation involves two consecutive chemical reactions:

The first reaction consists of a beta-elimination on the cystine caused by a hydroxide ion, resulting in the breaking of this bond and in the formation of dehydroalanine, as shown in the following reaction scheme.

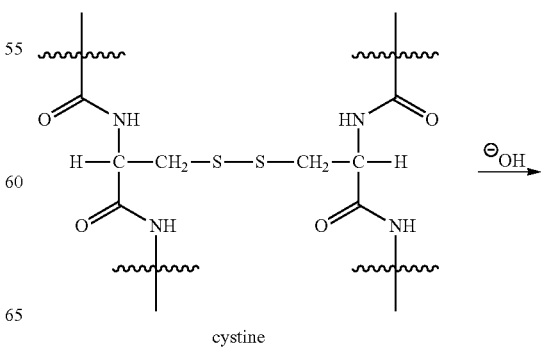

cystine

-continued

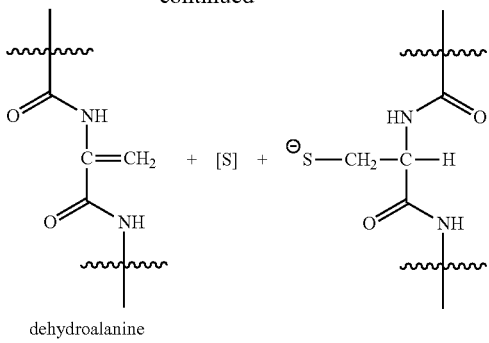
dehydroalanine

The second reaction is a reaction of the dehydroalanine with a thiol group. Specifically, the double bond of the dehydroalanine formed is a reactive double bond. It can react with the thiol group of the cysteine residue that was released to form a new bond known as a lanthionine bridge or bond or residue. This second reaction is illustrated by the following reaction scheme.

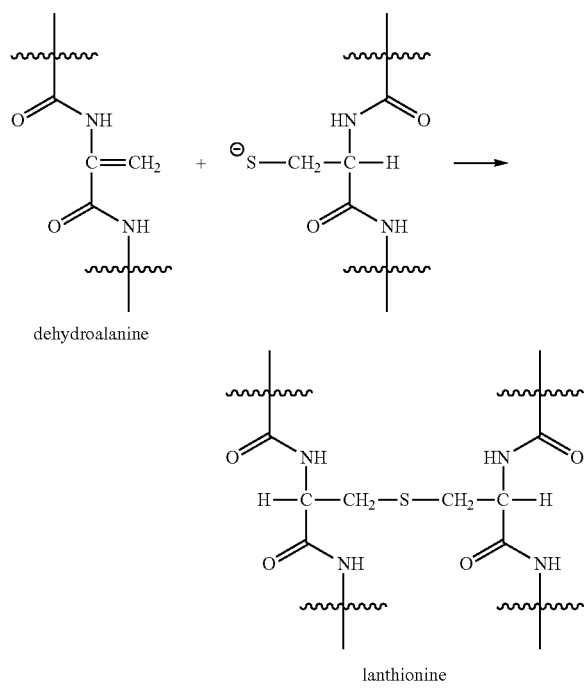

Compared with the first technique previously described, using a reducing agent, this lanthionization technique does not require a fixing step since the formation of the lanthionine bridges is irreversible. It is therefore performed in a single step and makes it possible without distinction either to wave the hair, or to shape or relax or straighten the hair. This technique is mainly used for shaping naturally frizzy hair.

However, the hydroxides employed during this process have the major drawback of being caustic. This causticity affects the scalp by causing irritation which is sometimes severe, and can also affect the condition of the hair by making it, on the one hand, rough to the touch and, on the other hand, much more brittle. The use of hydroxides can also in certain cases cause bleaching of the natural colour of the hair.

There is thus a real need to find novel compositions and to implement processes for the long-lasting straightening of keratin fibres, in particular human keratin fibres such as the hair, which do not have the set of drawbacks described above, i.e. which do not involve the use of alkaline active agents or reducing agents, and which afford long-lasting straightening of keratin fibres, while at the same time giving satisfactory capillary properties especially in terms of sheen and cosmeticity.

Furthermore, such compositions should have good working qualities, especially in terms of texture and viscosity and more particularly in terms of ease of spreading on the head of hair, of ease of blow-drying and of ease of passage of a heating device, for example flat tongs.

The Applicant has now found that the use of a keratin fibre straightening composition comprising (a) one or more compounds chosen from urea and/or urea derivatives, (b) one or more nonionic, cationic, amphoteric polymeric associative thickeners or anionic polymeric associative thickeners comprising one or more acrylic and/or methacrylic units makes it possible to achieve the desired long-lasting straightening properties, in particular when it is combined with the use of a heating means.

One subject of the present invention is thus a cosmetic composition comprising:
(a) at least 2% by weight, relative to the total weight of the composition, of one or more compounds chosen from urea and/or urea derivatives,
(b) one or more nonionic, cationic, amphoteric or anionic polymeric thickeners chosen from nonionic, cationic, amphoteric or anionic associative thickening polymers, the said anionic polymeric thickener(s) comprising one or more acrylic and/or methacrylic units.

The application to keratin fibres of this composition according to the present invention followed by the use of a heating means, at a temperature ranging from 25 to 250° C. in particular affords long-lasting straightening of keratin fibres without, however, having the drawbacks of straightening using strong alkaline agents or reducing agents.

Furthermore, the composition according to the invention has very good cosmetic qualities and very good working qualities.

Other characteristics and advantages of the invention will emerge more clearly on reading the description and the examples that follow.

As indicated previously, the composition according to the invention comprises:
(a) at least 2% by weight, relative to the total weight of the composition, of one or more compounds chosen from urea and/or urea derivatives,
(b) one or more nonionic, cationic, amphoteric or anionic polymeric thickeners chosen from nonionic, cationic, amphoteric or anionic associative thickening polymers, the said anionic polymeric thickener(s) comprising one or more acrylic and/or methacrylic units.

The term "urea derivative" means any compound other than urea $CO(NH_2)_2$ itself, comprising in its chemical formula a carbonyl group simply bonded to two nitrogen atoms, i.e. a unit

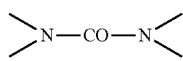

Preferably, the said compound(s) (a) are chosen from the compounds of formula (I) or (II), salts thereof or hydrates thereof:

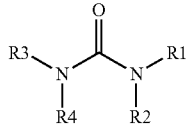
(I)

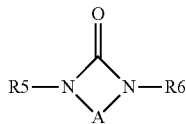
(II)

in which:
R1, R2, R3 and R4 represent, independently:
(i) a hydrogen atom or
(ii), a linear or branched, cyclic or acyclic $C_1$-$C_5$ lower alkyl or alkenyl radical, a $C_1$-$C_5$ alkoxy radical, a $C_6$-$C_{18}$ aryl radical, a 5- to 8-membered heterocyclic radical; these radicals being optionally substituted with a radical chosen from the following radicals: hydroxyl, (di)($C_1$-$C_4$)(alkyl) amino such as dimethylamino, carboxyl, halogen, $C_6$-$C_{18}$ aryl, carboxamide and N-methylcarboxamide;
it being understood that:
when R1, R2 and R3 represent a hydrogen atom, R4 may denote a carboxamide, methoxy, ethoxy, 1,2,4-triazolyl, cyclopentyl, ($C_1$-$C_6$)alkylcarbonyl such as acetyl, or ($C_1$-$C_6$)alkoxycarbonyl radical such as methoxycarbonyl or ethoxycarbonyl, —CO—CH=CH—COOH, phenyl optionally substituted with a chlorine atom or a hydroxyl, benzyl or 2,5-dioxo-4-imidazolidinyl radical;
when R1 and R3 represent a hydrogen atom, R2 may represent a hydrogen atom or a methyl or ethyl radical and R4 may represent an acetyl radical;
when R1=R2=H, R3 and R4 can form, with the nitrogen atom that bears them, a piperidine, 3-methylpyrazole, 3,5-dimethylpyrazole or maleimide ring;
R1 and R2 and also R3 and R4 can form, with the nitrogen atom that bears them, an imidazole ring;
R5 and R6 represent, independently of each other:
(iii) a hydrogen atom or
(iv) a linear or branched, cyclic or acyclic $C_1$-$C_5$ lower alkyl, acyl or alkenyl radical, a $C_1$-$C_5$ alkoxy radical, a $C_6$-$C_{18}$ aryl radical, a 5- to 8-membered heterocyclic radical; these radicals being optionally substituted with a radical chosen from the following radicals: hydroxyl, amino, dimethylamino, carboxyl, halogen, $C_6$-$C_{18}$ aryl, carboxamide and N-methylcarboxamide;
A is a radical chosen from the following radicals: $CH_2$—$CH_2$, CH=CH, $CH_2$—CO, CO—NH, CH=N, CO—CO, CHOH—CHOH, (HOOC)CH—CH, CHOH—CO, $CH_2$—$CH_2$—$CH_2$, $CH_2$—NH—CO, CH=C($CH_3$)—CO, NH—CO—NH, $CH_2$—$CH_2$—CO, $CH_2$—N($CH_3$)—$CH_2$, NH—$CH_2$—NH, CO—CH($CH_3$)—$CH_2$, CO—$CH_2$—CO, CO—NH—CO, CO—CH(COOH)—$CH_2$, CO—CH=C(COOH), CO—CH=C($CH_3$), CO—C($NH_2$)=CH, CO—C($CH_3$)=N, CO—CH=CH, CO—CH=N and CO—N=CH.
Among the compounds of formula (I) that are particularly preferred according to the invention, mention may be made of:

urea
methylurea
ethylurea
propylurea
n-butylurea
sec-butylurea
isobutylurea
tert-butylurea
cyclopentylurea
ethoxyurea
hydroxyethylurea
N-(2-hydroxypropyl)urea
N-(3-hydroxypropyl)urea
N-(2-dimethylaminopropyl)urea
N-(3-dimethylaminopropyl)urea
1-(3-hydroxyphenyl)urea
benzylurea
N-carbamoylmaleamide
N-carbamoylmaleamic acid
piperidinecarboxamide
1,2,4-triazol-4-ylurea
hydantoic acid
methyl allophanate
ethyl allophanate
acetylurea
hydroxyethyleneurea
2-(hydroxyethyl)ethyleneurea
diallylurea
chloroethylurea
N,N-dimethylurea
N,N-diethylurea
N,N-dipropylurea
cyclopentyl-1-methylurea
1,3-dimethylurea
1,3-diethylurea
1,3-bis(2-hydroxyethyl)urea
1,3-bis(2-hydroxypropyl)urea
1,3-bis(3-hydroxypropyl)urea
1,3-dipropylurea
ethyl-3-propylurea
sec-butyl-3-methylurea
isobutyl-3-methylurea
cyclopentyl-3-methylurea
N-acetyl-N'-methylurea
trimethylurea
butyl-3,3-dimethylurea
tetramethylurea and
benzylurea.
Among the compounds of formula (II) that are particularly preferred according to the invention, mention may be made of:
parabanic acid
2-dihydro-3H-1,2,4-triazol-2-one
barbituric acid
uracil
1-methyluracil
3-methyluracil
5-methyluracil
1,3-dimethyluracil
5-azauracil
6-azauracil
5-fluorouracil
6-fluorouracil
1,3-dimethyl-5-fluorouracil
5-aminouracil
6-aminouracil
6-amino-1-methyluracil 6-amino-1,3-dimethyluracil
4-chlorouracil
5-chlorouracil
5,6-dihydrouracil
5,6-dihydro-5-methyluracil
2-imidazolidone
1-methyl-2-imidazolidinone
1,3-dimethyl-2-imidazolidinone
4,5-dihydroxy-imidazolidin-2-one
1-(2-hydroxyethyl)-2-imidazolidinone
1-(2-hydroxypropyl)-2-imidazolidinone
1-(3-hydroxypropyl)-2-imidazolidinone
4,5-dihydroxy-1,3-dimethyl-imidazolidin-2-one
1,3-bis(2-hydroxyethyl)-2-imidazolidinone
2-imidazolidone-4-carboxylic acid
1-(2-aminoethyl)-2-imidazole
4-methyl-1,2,4-triazoline-3,5-dione
2,4-dihydroxy-6-methylpyrimidine
1-amino-4,5-dihydro-1H-tetrazol-5-one
hydantoin
1-methylhydantoin
5-methylhydantoin
5,5-dimethylhydantoin
5-ethylhydantoin
5-n-propylhydantoin
5-ethyl-5-methylhydantoin
5-hydroxy-5-methylhydantoin
5-hydroxymethylhydantoin
1-allylhydantoin
1-aminohydantoin
hydantoin-5-acetic acid
hexahydro-1,2,4,5-tetrazine-3,6-dione
5-methyl-1,3,5-triazinon-2-one
1-methyltetrahydropyrimidin-2-one
2,4-dioxohexahydro-1,3,5-triazine
urazole
4-methylurazole
orotic acid
dihydroxyorotic acid
2,4,5-trihydroxypyrimidine
2-hydroxy-4-methylpyrimidine
4,5-diamino-2,6-dihydroxypyrimidine
barbituric acid
1,3-dimethylbarbituric acid
cyanuric acid
1-methyl-hexahydropyrimidine-2,4-dione
1,3-dimethyl-3,4,5,6-tetrahydro-2-1H-pyrimidinone
5-(hydroxymethyl-2,4-(1H-3H)-pyrimidinedione
2,4-dihydroxypyrimidine-5-carboxylic acid
6-azathymine
5-methyl-1,3,5-triazinan-2-one
N-carbamoylmaleamic acid and
alloxan monohydrate.

Preferentially, the said compound(s) (a) are chosen from urea and hydroxyethylurea.

The said compound(s) (a) preferably represent from 2% to 50% by weight, more preferentially from 2% to 20% by weight, better still from 2% to 12% by weight and even better still from 2% to 10% by weight, relative to the total weight of the composition.

The composition according to the invention also comprises one or more nonionic, cationic, amphoteric associative polymeric thickeners or anionic associative polymeric thickeners comprising one or more acrylic and/or methacrylic units (b).

According to the present invention, the term "thickener" means compounds which, by their presence, increase the viscosity of the aqueous phase into which they are introduced by at least 20 cps and preferably by at least 50 cps, at 25° C. and at a shear rate of 1 s$^{-1}$ (the viscosity may be measured using a cone/plate viscometer, a Haake R600 rheometer or the like).

These nonionic, cationic, amphoteric associative polymeric thickeners or anionic associative polymeric thickeners comprising one or more acrylic and/or methacrylic units are preferably water-soluble or water-dispersible at a pH of 7 and at room temperature (25° C.).

The terms "water-soluble" and "water-dispersible" refer to a polymer which forms in water at a weight concentration of 0.1% at pH 7 and at room temperature (25° C.) a visually homogeneous (one-phase) medium.

The term "associative polymer" refers to polymers that are capable, in an aqueous medium, of reversibly combining with each other or with other molecules.

Associative polymers more particularly comprise at least one hydrophilic part and at least one hydrophobic part.

Thus, in particular, associative polymers comprise at least one hydrophobic group.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound.

By way of example, the hydrophobic group may be derived from a fatty alcohol such as stearyl alcohol, dodecyl alcohol or decyl alcohol. It may also denote a hydrocarbon-based polymer, for instance polybutadiene.

The associative thickening polymers that are used according to the invention are especially chosen from:
  (i) nonionic amphiphilic polymers comprising at least one fatty chain and at least one hydrophilic unit;
  (ii) cationic amphiphilic polymers comprising at least one hydrophilic unit and at least one fatty-chain unit;
  (iii) amphoteric amphiphilic polymers comprising at least one hydrophilic unit and at least one fatty-chain unit, the fatty chains containing from 10 to 30 carbon atoms.

The nonionic associative polymers are preferably chosen from:
  (1) celluloses modified with groups comprising at least one fatty chain; examples that may be mentioned include:
    hydroxyethylcelluloses modified with groups comprising at least one fatty chain, such as alkyl, arylalkyl or alkylaryl groups, or mixtures thereof, and in which the alkyl groups are preferably $C_8$-$C_{22}$, for instance the product Natrosol Plus Grade 330 CS ($C_{16}$ alkyls) sold by the company Aqualon, or the product Bermocoll EHM 100 sold by the company Berol Nobel,
    hydroxyethylcelluloses modified with alkylphenyl polyalkylene glycol ether groups, such as the product Amercell Polymer HM1500 (nonylphenyl polyethylene glycol (15) ether) sold by the company Amerchol,
  (2) hydroxypropyl guars modified with groups comprising at least one fatty chain, such as the product Esaflor HM 22 ($C_{22}$ alkyl chain) sold by the company Lamberti, and the products RE210-18 ($C_{14}$ alkyl chain) and RE205-1 ($C_{20}$ alkyl chain) sold by the company Rhodia,
  (3) copolymers of $C_1$-$C_6$ alkyl methacrylates or acrylates and of amphiphilic monomers comprising at least one fatty chain, for instance the oxyethylenated methyl acrylate/stearyl acrylate copolymer sold by the company Goldschmidt under the name Antil 208, (4) copolymers of hydrophilic methacrylates or acrylates and of hydrophobic monomers comprising at least one fatty chain, for instance the polyethylene glycol methacrylate/lauryl methacrylate copolymer, (5) polyurethane polyethers comprising in their chain both hydrophilic blocks usually of polyoxyethylenated nature and hydrophobic blocks, which may be aliphatic sequences alone and/or cycloaliphatic and/or aromatic sequences, (6) polymers with an aminoplast ether backbone bearing at least one fatty chain, such as the Pure Thin compounds sold by the company Sud-Chemie, (7) copolymers of vinylpyrrolidone and of fatty-chain hydrophobic monomers; examples that may be mentioned include:

the products Antaron V216 or Ganex V216 (vinylpyrrolidone/hexadecene copolymer) sold by the company ISP, the products Antaron V220 or Ganex V220 (vinylpyrrolidone/eicosene copolymer) sold by the company ISP.

Preferably, the polyurethane polyethers comprise at least two hydrocarbon-based lipophilic chains containing from 8 to 30 carbon atoms, separated by a hydrophilic block, the hydrocarbon-based chains possibly being pendent chains or chains at the end of the hydrophilic block. In particular, it is possible for one or more pendent chains to be envisaged. In addition, the polymer may comprise a hydrocarbon-based chain at one end or at both ends of a hydrophilic block.

The polyurethane polyethers may be multiblock, in particular in triblock form. The hydrophobic blocks may be at each end of the chain (for example: triblock copolymer containing a hydrophilic central block) or distributed both at the ends and in the chain (for example multiblock copolymer). These same polymers may also be graft polymers or star polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane bond between the hydrophilic blocks, whence arises the name.

By extension, also included among the nonionic fatty-chain polyurethane polyethers are those in which the hydrophilic blocks are linked to the lipophilic blocks via other chemical bonds.

As examples of fatty-chain nonionic polyurethane polyethers, use may also be made of Rheolate 205 containing a urea function, sold by the company Rheox, or Rheolate 208, 204 or 212, and also Acrysol RM 184, Aculyn 44 and Aculyn 46 from the company Röhm & Haas [Aculyn 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44 is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Mention may also be made of the product Elfacos T210 containing a $C_{12}$-$C_{14}$ alkyl chain, and the product Elfacos T212 containing a $C_{18}$ alkyl chain, from Akzo.

The product DW 1206B from Röhm & Haas containing a $C_{20}$ alkyl chain and a urethane bond, sold at a solids content of 20% in water, may also be used.

Use may also be made of solutions or dispersions of these polymers, especially in water or in aqueous-alcoholic medium. Examples of such polymers that may be mentioned are Rheolate 255, Rheolate 278 and Rheolate 244 sold by the company Rheox. Use may also be made of the products DW 1206F and DW 1206J sold by the company Röhm & Haas.

The polyurethane polyethers that may be used according to the invention are in particular those described in the article by G. Fonnum, J. Bakke and Fk. Hansen—Colloid Polym. Sci 271, 380.389 (1993).

The cationic associative polymers are preferably chosen from:

(A') cationic associative polyurethanes, the family of which has been described by the Applicant in French patent application No. 00/09609; it may be represented by the general formula (Ia) below:

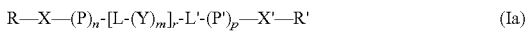

$$R\text{—}X\text{—}(P)_n\text{-}[L\text{-}(Y)_m]_r\text{-}L'\text{-}(P')_p\text{—}X'\text{—}R' \quad \text{(Ia)}$$

in which:

R and R', which may be identical or different, represent a hydrophobic group or a hydrogen atom;

X and X', which may be identical or different, represent a group comprising an amine function optionally bearing a hydrophobic group, or alternatively a group L";

L, L' and L", which may be identical or different, represent a group derived from a diisocyanate;

P and P', which may be identical or different, represent a group comprising an amine function optionally bearing a hydrophobic group;

Y represents a hydrophilic group;

r is an integer between 1 and 100 inclusive, preferably between 1 and 50 inclusive and in particular between 1 and 25 inclusive;

n, m and p are each, independently of each other, between 0 and 1000 inclusive;

the molecule containing at least one protonated or quaternized amine function and at least one hydrophobic group, In one preferred embodiment of these polyurethanes, the only hydrophobic groups are the groups R and R' at the chain ends.

One preferred family of cationic associative polyurethanes is the one corresponding to formula (la) described above and in which:

R and R' both independently represent a hydrophobic group,

X and X' each represent a group L", n and p are integers that are between 1 and 1000 inclusive, and L, L', L", P, P', Y and m have the meaning given above.

Another preferred family of cationic associative polyurethanes is the one corresponding to formula (Ia) above in which:

the fact that n and p are 0 means that these polymers do not comprise units derived from a monomer containing an amine function, incorporated into the polymer during the polycondensation.

the protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above and Q denotes a leaving group such as a halide, a sulfate, etc.

Yet another preferred family of cationic associative polyurethanes is the one corresponding to formula (Ia) above in which:

R and R' both independently represent a hydrophobic group,

X and X' both independently represent a group comprising a quaternary amine, n and p are zero, and L, L', Y and m have the meaning given above.

The number-average molecular mass of the cationic associative polyurethanes is preferably between 400 and 500 000 inclusive, in particular between 1000 and 400 000 inclusive and ideally between 1000 and 300 000 inclusive.

The expression "hydrophobic group" means a radical or polymer containing a saturated or unsaturated, linear or branched hydrocarbon-based chain, which may contain one or more heteroatoms such as P, O, N or S, or a radical containing a perfluoro or silicone chain. When the hydrophobic group denotes a hydrocarbon-based radical, it comprises at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound.

By way of example, the hydrophobic group may be derived from a fatty alcohol such as stearyl alcohol, dodecyl alcohol or decyl alcohol. It may also denote a hydrocarbon-based polymer, for instance polybutadiene.

When X and/or X' denote(s) a group comprising a tertiary or quaternary amine, X and/or X' may represent one of the following formulae:

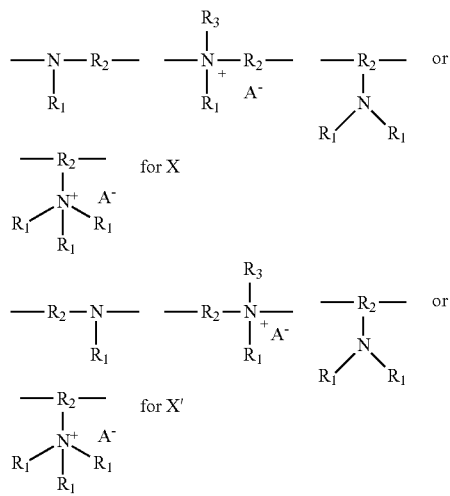

in which:

$R_2$ represents a linear or branched alkylene radical containing from 1 to 20 carbon atoms, optionally comprising a saturated or unsaturated ring, or an arylene radical, one or more of the carbon atoms possibly being replaced with a heteroatom chosen from N, S, O and P;

$R_1$ and $R_3$, which may be identical or different, denote a linear or branched $C_1$-$C_{30}$ alkyl or alkenyl radical or an aryl radical, at least one of the carbon atoms possibly being replaced with a heteroatom chosen from N, S, O and P;

$A^-$ is a physiologically acceptable anionic counterion such as a halide, for instance chloride or bromide, or mesylate.

The groups L, L' and L" represent a group of formula:

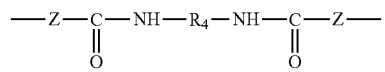

in which:

Z represents —O—, —S— or —NH—; and $R_4$ represents a linear or branched alkylene radical containing from 1 to 20 carbon atoms, optionally comprising a saturated or unsaturated ring, or an arylene radical, one or more of the carbon atoms possibly being replaced with a heteroatom chosen from N, S, O and P.

The groups P and P' comprising an amine function may represent at least one of the following formulae:

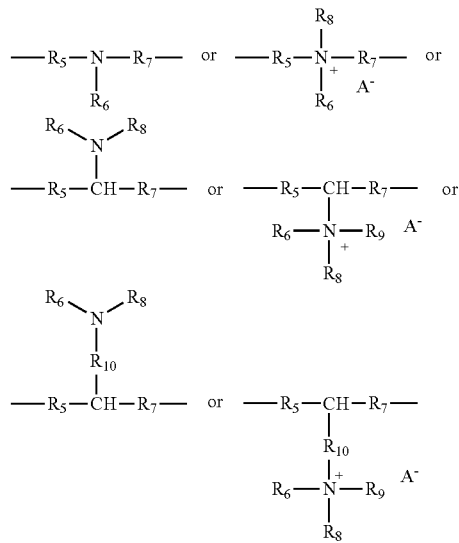

in which:

$R_5$ and $R_7$ have the same meanings as $R_2$ defined above;

$R_6$, $R_8$ and $R_9$ have the same meanings as $R_1$ and $R_3$ defined above;

$R_{10}$ represents a linear or branched, optionally unsaturated alkylene group possibly containing one or more heteroatoms chosen from N, O, S and P; and $A^-$ is a physiologically acceptable anionic counterion such as a halide, for instance chloride or bromide, or mesylate.

As regards the meaning of Y, the term "hydrophilic group" means a polymeric or non-polymeric water-soluble group.

By way of example, when it is not a polymer, mention may be made of ethylene glycol, diethylene glycol and propylene When it is a hydrophilic polymer, in accordance with one preferred embodiment, mention may be made, for example, of polyethers, sulfonated polyesters, sulfonated polyamides or a mixture of these polymers. The hydrophilic compound is preferentially a polyether and especially a poly(ethylene oxide) or poly(propylene oxide).

The cationic associative polyurethanes of formula (Ia) according to the invention are formed from diisocyanates and from various compounds bearing functions containing a labile hydrogen. The functions containing a labile hydrogen may be alcohol, primary or secondary amine or thiol functions, giving, after reaction with the diisocyanate functions, polyurethanes, polyureas and polythioureas, respectively. In the present invention, the term "polyurethanes" encompasses these three types of polymer, namely polyurethanes per se, polyureas and polythioureas, and also copolymers thereof.

A first type of compound involved in the preparation of the polyurethane of formula (Ia) is a compound comprising at least one unit bearing an amine function. This compound may be multifunctional, but the compound is preferentially difunctional, that is to say that, according to one preferential embodiment, this compound comprises two labile hydrogen atoms borne, for example, by a hydroxyl, primary amine, secondary amine or thiol function. A mixture of multifunctional and difunctional compounds in which the percentage of multifunctional compounds is low may also be used, As mentioned above, this compound may comprise more than one unit containing an amine function. In this case, it is a polymer bearing a repetition of the unit containing an amine function, Compounds of this type may be represented by one of the following formulae:

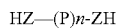
HZ—(P)n-ZH or

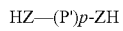
HZ—(P')p-ZH in which Z, P, P', n and p are as defined above.

Examples of compounds containing an amine function that may be mentioned include N-methyldiethanolamine, N-tert-butyldiethanolamine and N-sulfoethyldiethanolamine.

The second compound included in the preparation of the polyurethane of formula (Ia) is a diisocyanate corresponding to the formula:

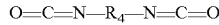
O=C=N—R$_4$—N=C=O in which R$_4$ is defined above.

By way of example, mention may be made of methylenediphenyl diisocyanate, methylenecyclohexane diisocyanate, isophorone diisocyanate, tolylene diisocyanate, naphthalene diisocyanate, butane diisocyanate and hexane diisocyanate.

A third compound involved in the preparation of the polyurethane of formula (Ia) is a hydrophobic compound intended to form the terminal hydrophobic groups of the polymer of formula (Ia).

This compound is formed from a hydrophobic group and a function containing a labile hydrogen, for example a hydroxyl, primary or secondary amine, or thiol function.

By way of example, this compound may be a fatty alcohol such as, in particular, stearyl alcohol, dodecyl alcohol or decyl alcohol. When this compound comprises a polymer chain, it may be, for example, α-hydroxylated hydrogenated polybutadiene.

The hydrophobic group of the polyurethane of formula (Ia) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, in which R and R' are as defined above and Q denotes a leaving group such as a halide, a sulfate, etc.

The cationic associative polyurethane may also comprise a hydrophilic block. This block is provided by a fourth type of compound involved in the preparation of the polymer. This compound may be multifunctional. It is preferably difunctional. It is also possible to have a mixture in which the percentage of multifunctional compound is low.

The functions containing a labile hydrogen are alcohol, primary or secondary amine or thiol functions. This compound may be a polymer terminated at the chain ends with one of these functions containing a labile hydrogen.

By way of example, when it is not a polymer, mention may be made of ethylene glycol, diethylene glycol and propylene glycol.

When it is a hydrophilic polymer, mention may be made, for example, of polyethers, sulfonated polyesters and sulfonated polyamides, or a mixture of these polymers. The hydrophilic compound is preferentially a polyether and especially a poly(ethylene oxide) or poly(propylene oxide).

The hydrophilic group termed Y in formula (Ia) is optional. Specifically, the units containing a quaternary amine or protonated function may suffice to provide the solubility or water-dispersibility required for this type of polymer in an aqueous solution.

Although the presence of a hydrophilic group Y is optional, cationic associative polyurethanes comprising such a group are, however, preferred, (B') quaternized cellulose derivatives.

The quaternized cellulose derivatives are, in particular:

i) quaternized celluloses modified with groups comprising at least one fatty chain, such as linear or branched alkyl, linear or branched arylalkyl or linear or branched alkylaryl groups comprising at least 8 carbon atoms, or mixtures thereof;

ii) quaternized hydroxyethylcelluloses modified with groups comprising at least one fatty chain, such as linear or branched alkyl, linear or branched arylalkyl or linear or branched alkylaryl groups comprising at least 8 carbon atoms, or mixtures thereof;

iii) the hydroxyethylcelluloses of formula (Ib):

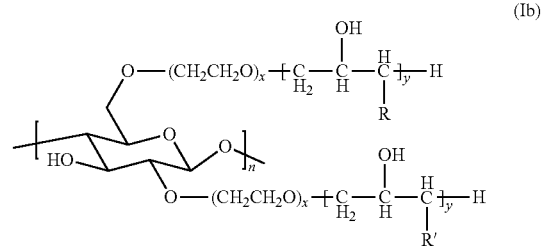

(Ib)

in which formula (Ib):

R and R', which may be identical or different, represent an ammonium group such as RaRbRcN$^+$—, Q$^-$ in which Ra, Rb and Rc, which may be identical or different, represent a hydrogen atom or a linear or branched C$_1$-C$_{30}$ and preferentially C$_1$-C$_{20}$ alkyl group, such as methyl or dodecyl; and Q$^-$ represents an anionic counterion such as a halide, for instance a chloride or bromide;

n, x and y, which may be identical or different, represent an integer between 1 and 10 000.

The alkyl radicals borne by the above quaternized celluloses i) or hydroxyethylcelluloses ii) preferably comprise from 8 to 30 carbon atoms. The aryl radicals preferably denote phenyl, benzyl, naphthyl or anthryl groups.

Examples of quaternized alkylhydroxyethylcelluloses containing C$_8$-C$_{30}$ fatty chains that may be indicated include the products Quatrisoft LM 200®, Quatrisoft LM-X 529-18-A®, Quatrisoft LM-X 529-18B® (C$_{12}$ alkyl) and Quatrisoft LM-X 529-8® (C$_{18}$ alkyl) sold by the company Amerchol, and the products Crodacel QM®, Crodacel QL® ($C_{12}$ alkyl) and Crodacel QS® ($C_{18}$ alkyl) sold by the company Croda.

Mention may also be made of the hydroxyethylcelluloses of formula (Ib) in which R represents a trimethylammonium halide and R' represents a dimethyldodecylammonium halide, more preferentially R represents trimethylammonium chloride $(CH_3)_3N^+ Cl^-$ and R' represents dimethyldodecylammonium chloride $(CH_3)_2(C_{12}H_{25})N^+ Cl^-$. Polymers of this type are known under the trade name Softcat Polymer SL®, such as SL-100 and SL-60.

More particularly, the polymers of formula (Ib) are those whose viscosity is between 2000 and 3000 cPs inclusive. Preferentially, the viscosity is between 2700 and 2800 cPs inclusive.

(C') Cationic polyvinyllactams, the family of which has been described by the Applicant in French patent application No. 01/01106.

The said polymers comprise:
a) at least one monomer of vinyllactam or alkylvinvl-lactam type;
b) at least one monomer of structure (Ic) or (IIc) below:

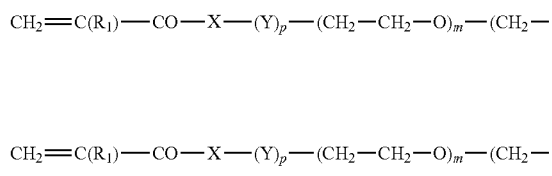

in which formulae (Ic) and (IIc):
X denotes an oxygen atom or a radical $NR_6$,
$R_1$ and $R_6$ denote, independently of each other, a hydrogen atom or a linear or branched $C_1$-$C_5$ alkyl radical,
$R_2$ denotes a linear or branched $C_1$-$C_4$ alkyl radical,
$R_3$, $R_4$ and $R_5$ denote, independently of each other, a hydrogen atom, a linear or branched $C_1$-$C_{30}$ alkyl radical or a radical of formula (IIIc):

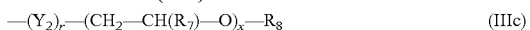

Y, $Y_1$ and $Y_2$ denote, independently of each other, a linear or branched $C_2$-$C_{16}$ alkylene radical,
$R_7$ denotes a hydrogen atom or a linear or branched $C_1$-$C_4$ alkyl radical or a linear or branched $C_1$-$C_4$ hydroxyalkyl radical,
$R_8$ denotes a hydrogen atom or a linear or branched $C_1$-$C_{30}$ alkyl radical,
p, q and r denote, independently of each other, either the value 0 or the value 1,
m and n denote, independently of each other, an integer ranging from 0 to 100 inclusive,
x denotes an integer ranging from 1 to 100 inclusive,
Z denotes an anionic counterion of an organic or mineral acid, such as a halide, for instance chloride or bromide, or mesylate;
with the proviso that:
at least one of the substituents $R_3$, $R_4$, $R_5$ or $R_8$ denotes a linear or branched $C_9$-$C_{30}$ alkyl radical,
if m or n is other than zero, then q is equal to 1,
if m or n is equal to zero, then p or q is equal to 0.

The cationic poly(vinylactam) polymers which may be used according to the invention may be crosslinked or noncrosslinked and may also be block polymers.

Preferably, the counterion $Z^-$ of the monomers of formula (Ic) is chosen from halide ions, phosphate ions, the methosulfate ion and the tosylate ion.

Preferably, $R_3$, $R_4$ and $R_5$ denote, independently of each other, a hydrogen atom or a linear or branched $C_1$-$C_{30}$ alkyl radical.

More preferentially, the monomer b) is a monomer of formula (Ic) for which, even more preferentially, in and n are equal to 0.

The vinyllactam or alkylvinvllactam monomer is preferably a compound of structure (IVc):

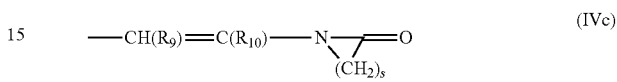

in which:
s denotes an integer ranging from 3 to 6,
$R_9$ denotes a hydrogen atom or a linear or branched $C_1$-$C_5$ alkyl radical,
$R_{10}$ denotes a hydrogen atom or a linear or branched $C_1$-$C_5$ alkyl radical,
with the proviso that at least one of the radicals $R_9$ and $R_{10}$ denotes a hydrogen atom.

Even more preferentially, the monomer (IVc) is vinylpyrrolidone.

The cationic poly(vinyllactam) polymers which may be used according to the invention may also contain one or more additional monomers, preferably cationic or nonionic monomers.

As compounds that are more particularly preferred according to the invention, mention may be made of the following terpolymers comprising at least:
a) one monomer of formula (IVc),
b) one monomer of formula (Ic) in which p=1, q=0, $R_3$ and $R_4$ denote, independently of each other, a hydrogen atom or a $C_1$-$C_5$ alkyl radical and $R_5$ denotes a linear or branched $C_9$-$C_{24}$ alkyl radical, and
c) one monomer of formula (IIc) in which $R_3$ and $R_4$ denote, independently of each other, a hydrogen atom or a linear or branched $C_1$-$C_5$ alkyl radical.

Even more preferentially, terpolymers comprising, by weight, 40% to 95% of monomer a), 0.1% to 55% of monomer c) and 0.25% to 50% of monomer b) will be used.

Such polymers are described in patent application WO 00/68282, the content of which forms an integral part of the invention.

As cationic poly(vinyllactam) polymers which may be used according to the invention, vinylpyrrolidone/dimethylaminopropylmethacrylamide/dodecyldimeth ylmethacrylamidopropylammonium tosylate terpolymers, vinyipyrrolidone/dimethylaminopropylmethacrylamide/cocoyldimethyl methacrylamidopropylammonium tosylate terpolymers, vinylpyrrolidone/dimethylaminopropylmethacrylamide/lauryldimethyl methacrylamidopropylammonium tosylate or chloride terpolymers are used in particular.

The weight-average molecular mass of the cationic poly(vinyllactam) polymers which may be used according to the present invention is preferably between 500 and 20 000 000. It is more particularly between 200 000 and 2 000 000 and even more preferentially between 400 000 and 800 000.

The amphoteric associative polymers are preferably chosen from those comprising at least one non-cyclic cationic unit. Even more particularly, the ones that are preferred are those prepared from or comprising 1 mol % to 20 mol %, preferably 1.5 mol % to 15 mol % and even more particularly 1.5 mol % to 6 mol % of fatty-chain monomer relative to the total number of moles of monomers.

The amphoteric associative polymers according to the invention comprise those that are prepared by copolymerizing:

1) at least one monomer of formula (Va) or (Vb):

$$R_1-\underset{H}{\overset{}{C}}=\underset{R_2}{\overset{}{C}}-\underset{O}{\overset{}{C}}-Z-(C_nH_{2n})-\underset{R_4}{\overset{R_3}{\overset{|}{N^+}}}-R_5 \quad A^-  \quad (Va)$$

$$R_1-\underset{H}{\overset{}{C}}=\underset{R_2}{\overset{}{C}}-\underset{O}{\overset{}{C}}-Z-(C_nH_{2n})-N\underset{R_4}{\overset{R_3}{\diagdown}} \quad (Vb)$$

in which $R_1$ and $R_2$, which may be identical or different, represent a hydrogen atom or a methyl radical, $R_3$, $R_4$ and $R_5$, which may be identical or different, represent a linear or branched alkyl radical containing from 1 to 30 carbon atoms, Z represents an NH group or an oxygen atom, n is an integer from 2 to 5, $A^-$ is an anion derived from an organic or mineral acid, such as a methosulfate anion or a halide such as chloride or bromide;

2) at least one monomer of formula (VI):

$$R_6-CH=CR_7-COOH \quad (VI)$$

in which $R_6$ and $R_7$, which may be identical or different, represent a hydrogen atom or a methyl radical; and 3) at least one monomer of formula (VII):

$$R_6-CH=CR_7-COXR_8 \quad (VII)$$

in which $R_6$ and $R_7$, which may be identical or different, represent a hydrogen atom or a methyl radical, X denotes an oxygen or nitrogen atom and $R_8$ denotes a linear or branched alkyl radical containing from 1 to 30 carbon atoms;

at least one of the monomers of formula (Va), (Vb) or (VII) comprising at least one fatty chain.

The monomers of formulae (Va) and (Vb) of the present invention are preferably chosen from the group formed by:
dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate,
dimethylaminopropylmethacrylamide, dimethylaminopropylacrylamide,
these monomers optionally being quaternized, for example with a $C_1$-$C_4$ alkyl halide or a $C_1$-$C_4$ dialkyl sulfate.

More particularly, the monomer of formula (Va) is chosen from acrylamidopropyltrimethylammonium chloride and methacrylamidopropyltrimethylammonium chloride.

The monomers of formula (VI) of the present invention are preferably chosen from the group formed by acrylic acid, methacrylic acid, crotonic acid and 2-methylcrotonic acid. More particularly, the monomer of formula (VI) is acrylic acid.

The monomers of formula (VII) of the present invention are preferably chosen from the group formed by $C_{12}$-$C_{22}$ and more particularly $C_{16}$-$C_{18}$ alkyl acrylates or methacrylates.

The monomers constituting the fatty-chain amphoteric polymers of the invention are preferably already neutralized and/or quaternized.

The ratio of the number of cationic charges/anionic charges is preferably equal to about 1.

The amphoteric associative polymers according to the invention preferably comprise from 1 mol % to 10 mol % of the monomer comprising a fatty chain (monomer of formula (Va), (Vb) or (VII)), and preferably from 1.5 mol % to 6 mol %.

The amphoteric associative polymers according to the invention may also contain other monomers such as nonionic monomers and in particular such as $C_1$-$C_4$ alkyl acrylates or methacrylates.

Amphoteric associative polymers according to the invention are described and prepared, for example, in patent application WO 98/44012.

Among the amphoteric associative polymers according to the invention, the ones that are preferred are acrylic acid/(meth)acrylamidopropylmethylammonium chloride/stearyl methacrylate terpolymers.

The preferred associative polymers are chosen from nonionic and cationic polymers.

Preferably, the associative polymers of the invention are celluloses or polyurethanes, and preferably celluloses.

The polymeric thickeners (b) that are used according to the invention may also be chosen from anionic associative polymeric thickeners containing acrylic and/or methacrylic units.

The (meth)acrylic anionic associative thickeners that may be used according to the invention may be chosen from those comprising at least one hydrophilic unit of unsaturated olefinic carboxylic acid type, and at least one hydrophobic unit of the type such as a ($C_{10}$-$C_{30}$)alkyl ester of an unsaturated carboxylic acid.

More particularly, these (meth)acrylic associative thickeners are preferably chosen from those in which the hydrophilic unit of unsaturated olefinic carboxylic acid type corresponds to the monomer of formula (VIII) below:

$$H_2C=\underset{R^1}{\overset{}{C}}-\underset{O}{\overset{}{C}}-OH \quad (VIII)$$

in which formula $R^1$ denotes H or $CH_3$, i.e. acrylic acid or methacrylic acid units, and in which the hydrophobic unit of ($C_{10}$-$C_{30}$)alkyl ester of unsaturated carboxylic acid type corresponds to the monomer of formula (IX) below:

$$H_2C=\underset{R^1}{\overset{}{C}}-\underset{O}{\overset{}{C}}-OR^2 \quad (IX)$$

in which formula $R^1$ denotes H or $CH_3$ (i.e. acrylate or methacrylate units), $R^2$ denoting a $C_{10}$-$C_{30}$ and preferably $C_{12}$-$C_{22}$ alkyl radical.

As ($C_{10}$-$C_{30}$)alkyl esters of unsaturated carboxylic acids according to formula (IX), mention may be made more particularly of lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

(Meth)acrylic associative thickeners of this type are described and prepared, for example, according to U.S. Pat. Nos. 3,915,921 and 4,509,949.

The (meth)acrylic associative thickeners that may be used according to the invention may more particularly denote polymers formed from a mixture of monomers comprising:

(i) acrylic acid and one or more esters of formula (X) below:

(X)

in which $R^3$ denotes H or $CH_3$, $R^4$ denoting an alkyl radical having from 12 to 22 carbon atoms, and optionally a crosslinking agent, for instance those consisting of from 95% to 60% by weight of acrylic acid (hydrophilic unit), 4% to 40% by weight of $C_{10}$-$C_{30}$ alkyl acrylate (hydrophobic unit), and 0 to 6% by weight of crosslinking polymerizable monomer, or 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polyrnerizable monomer; or (ii) essentially acrylic acid and lauryl methacrylate, such as the product formed from 66% by weight of acrylic acid and 34% by weight of lauryl methacryiate.

For the purposes of the invention, the term "crosslinking agent" means a monomer containing a group

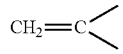

and at least one other polymerizable group, the unsaturated bonds of the monomer being unconjugated relative to each other.

As crosslinking agent that may be used according to the invention, mention may be made especially of polyallyl ethers especially such as polyallyl sucrose and polyallylpentaerythritol.

Among the said (meth)acrylic associative thickeners above, the ones most particularly preferred according to the present invention are the products sold by the company Goodrich under the trade names Pemulen TR1, Pemulen TR2, Carbopol 1382, and more preferably still Pemulen TR1, and the product sold by the company S.E.P.C. under the name Coatex SX.

As (meth)acrylic associative thickeners, mention may also be made of the copolymer of methacrylic acid/methyl acrylate/dimethyl-meta-isopropenylbenzyl isocyanate of ethoxylated alcohol sold under the name Viscophobe DB 1000 by the company Amerchol.

Other (meth)acrylic associative thickeners that may be used according to the invention may also be sulfonic polymers comprising at least one (meth)acrylic monomer bearing sulfonic group(s), in free form or partially or totally neutralized form and comprising at least one hydrophobic portion.

The said hydrophobic portion present in the said sulfonic polymers that may be used according to the invention preferably comprises from 8 to 22 carbon atoms, more preferably still from 8 to 18 carbon atoms and more particularly from 12 to 18 carbon atoms.

Preferentially, these sulfonic polymers that may be used according to the invention are partially or totally neutralized with a mineral base (sodium hydroxide, potassium hydroxide or aqueous ammonia) or an organic base such as mono-, di- or triethanolamine, an aminomethylpropanediol, N-methylglucamine, basic amino acids, for instance arginine and lysine, and mixtures of these compounds.

These said sulfonic polymers generally have a number-average molecular weight ranging from 1000 to 20 000 000 g/mol, preferably ranging from 20 000 to 5 000 000 and even more preferably from 100 000 to 1 500 000 g/mol.

The sulfonic polymers that may be used according to the invention may or may not be crosslinked. Crosslinked polymers are preferably chosen.

When they are crosslinked, the crosslinking agents may be selected from polyolefinically unsaturated compounds commonly used for the crosslinking of polymers obtained by free-radical polymerization. Mention may be made, for example, of divinylbenzene, diallyl ether, dipropylene glycol diallyl ether, polyglycol diallyl ethers, triethylene glycol divinyl ether, hydroquinone diallyl ether, ethylene glycol diacrylatedi(meth)acrylate or tetraethylene glycol diacrylatedi(meth)acrylate, trimethylolpropane triacrylate, methylenebisacrylamide, methylenebismethacrylamide, triallylamine, triallyl cyanurate, diallyl maleate, tetraalyethylenediamine, tetraallyloxyethane, trimethylolpropane diallyl ether, allyl (meth)acrylate, allyl ethers of alcohols of the sugar series, or other allyl or vinyl ethers of polyfunctional alcohols, and also allyl esters of phosphoric and/or vinylphosphonic acid derivatives, or mixtures of these compounds.

Methylenebisacrylamide, allyl methacrylate or trimethylolpropane triacrylate (TMPTA) will be used more particularly.

The degree of crosslinking will generally range from 0.01 mol % to 10 mol % and more particularly from 0.2 mol % to 2 mol % relative to the polymer.

The (meth)acrylic monomers bearing sulfonic group(s) of the sulfonic polymers that may be used according to the invention are chosen especially from (meth)acrylamido($C_1$-$C_{22}$)alkylsulfonic acids and N-($C_1$-$C_{22}$)alkyl(meth)acrylamido($C_1$-$C_{22}$)alkylsulfonic acids, for instance undecylacrylamidomethanesulfonic acid, and also partially or totally neutralized forms thereof.

(Meth)acrylamido($C_1$-$C_{22}$)alkylsulfonic acids, for instance acrylamidomethanesulfonic acid, acrylamidoethanesufonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, will more preferentially be used.

2-Acrylamido-2-methylpropanesulfonic acid (AMPS), and also partially or totally neutralized forms thereof, will even more particularly be used.

The (meth)acrylic associative thickeners that may be used according to the invention may be chosen especially from random amphiphilic AMPS polymers modified by reaction with a $C_6$-$C_{22}$ n-monoalkylamine or $C_6$-$C_{22}$ di-n-alkylamine, and such as those described in patent application WO 00/31154 (which forms an integral part of the content of the description). These polymers may also contain other ethylenically unsaturated hydrophilic monomers selected, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The (meth)acrylic associative thickeners bearing sulfonic group(s) that may particularly preferably be used according to the invention are preferably chosen from amphiphilic copolymers of AMPS and of at least one ethylenically unsaturated hydrophobic monomer comprising at least one hydrophobic portion containing from 8 to 50 carbon atoms, more preferably from 8 to 22 carbon atoms, more preferably still from 8 to 18 carbon atoms and more particularly 12 to 18 carbon atoms.

These same copolymers may also contain one or more ethylenically unsaturated monomers not comprising a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in patent application EP-A-750 899, U.S. Pat. No. 5,089,578 and in the following Yotaro Morishima publications:

Self-assembling amphiphilic polyelectrolytes and their nanostructures, Chinese Journal of Polymer Science, Vol. 18, No. 40, (2000), 323-336;

Micelle formation of random copolymers of sodium 2-(acrylamido)-2-methylpropanesulfonate and a nonionic surfactant macromonomer in water as studied by fluorescence and dynamic light scattering, Macromolecules, 2000, Vol. 33, No. 10-3694-3704;

Solution properties of micelle networks formed by nonionic moieties covalently bound to a polyelectrolyte: salt effects on rheological behavior—Langmuir, 2000, Vol. 16, No. 12, 5324-5332;

Stimuli responsive amphiphilic copolymers of sodium 2-acrylamido)-2-methylpropanesulfonate and associative macromonomers, Polym. Preprint, Div. Polym. Chem. 1999, 40(2), 220-221.

The ethylenically unsaturated hydrophobic monomers of these particular copolymers are preferably selected from the acrylates or acrylamides of formula (XI) below:

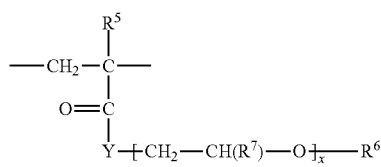

(XI)

in which $R^5$ and $R^7$, which may be identical or different, denote a hydrogen atom or a linear or branched $C_1$-$C_6$ alkyl radical (preferably methyl); Y denotes O or NH; $R^6$ denotes a hydrophobic hydrocarbon-based radical containing at least 8 to 50 carbon atoms, more preferentially from 8 to 22 carbon atoms, even more preferentially from 6 to 18 carbon atoms and more particularly from 12 to 18 carbon atoms; x denotes a number of moles of alkylene oxide and ranges from 0 to 100.

The radical $R^6$ is preferably chosen from linear $C_6$-$C_{18}$ alkyl radicals (for example n-hexyl, n-octyl, n-decyl, n-hexadecyl, n-dodecyl), or branched or cyclic $C_6$-$C_{18}$ alkyl radicals (for example cyclododecane ($C_{12}$) or adamantane ($C_{10}$)); $C_6$-$C_{18}$ perfluoroalkyl radicals (for example the group of formula —$(CH_2)_2$—$(CF_2)_9$—$CF_3$); the cholesteryl radical ($C_{27}$) or a cholesterol ester residue, for instance the cholesteryl oxyhexanoate group; aromatic polycyclic groups such as naphthalene or pyrene. Among these radicals, the ones that are more particularly preferred are linear alkyl radicals and more particularly the n-dodecyl radical.

According to a particularly preferred form of the invention, the monomer of formula (XI) comprises at least one alkylene oxide unit (x≥1) and preferably a polyoxyalkylene chain. The polyoxyalkylene chain preferentially consists of ethylene oxide units and/or propylene oxide units and even more particularly consists of ethylene oxide units. The number of oxyalkylene units generally ranges from 3 to 100, more preferably from 3 to 50 and more preferably still from 7 to 25.

Among these polymers, mention may be made of:

copolymers, which may or may not be crosslinked and which may or may not be neutralized, comprising from 15% to 60% by weight of AMPS units and from 40% to 85% by weight of ($C_8$-$C_{16}$)alkyl(meth)acrylamide units or of ($C_8$-$C_{16}$)alkyl (meth)acrylate units, relative to the polymer, such as those described in patent application EP-A-750 899;

terpolymers comprising from 10 mol % to 90 mol % of acrylamide units, from 0.1 mol % to 10 mol % of AMPS units and from 5 mol % to 80 mol % of n-($C_6$-$C_{18}$)alkylacrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Mention will be made more particularly of the copolymers constituted of 2-acrylamido-2-methylpropanesulfonic acid (AMPS) units of formula (XII) below:

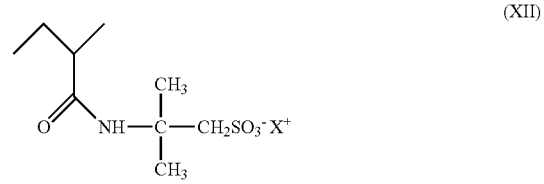

(XII)

in which $X^+$ is a proton, an alkali metal cation, an alkaline-earth metal cation or an ammonium ion;
and units of formula (XIII) below:

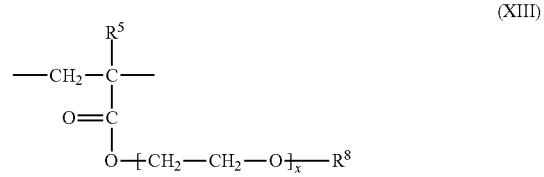

(XIII)

in which x denotes an integer ranging from 3 to 100, preferably from 5 to 80 and more preferentially from 7 to 25; $R^5$ has the same meaning as that indicated above in formula (XI) and $R^8$ denotes a linear or branched $C_6$-$C_{22}$ and more preferentially $C_{10}$-$C_{22}$ alkyl.

The polymers that are particularly preferred are those for which x=25, $R^5$ denotes methyl and $R^8$ represents n-dodecyl; they are described in the Morishima articles mentioned above.

The polymers for which $X^+$ denotes sodium or ammonium are more particularly preferred.

The nonionic, cationic, amphoteric or anionic associative polymeric thickening polymer(s) (b) may be present in the composition according to the invention in a content ranging from 0.01% to 30% by weight, preferably from 0.1% to 20% by weight and better still from 0.2% to 10% by weight relative to the total weight of the composition.

The composition according to the invention may also comprise one or more thickeners other than the associative polymeric thickeners already mentioned.

The composition according to the invention may also comprise one or more surfactants, more particularly nonionic, anionic, cationic or amphoteric surfactants.

The nonionic surfactant(s) that may be used in the cosmetic composition according to the invention are described, for example, in the *Handbook of Surfactants* by M. R. Porter, published by Blackie & Son (Glasgow and London), 1991, pp. 116-178. They are especially chosen from alcohols, α-diols and ($C_1$-$C_{20}$)alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, polyoxyalkylenated fatty acid esters, optionally oxyalkylenated alkylpolyglycosides, alkyl glucoside esters, N-alkylglucamine and N-acyl-methylglucamine derivatives, aldobionamides, oxyethylenated oils and amine oxides.

Unless otherwise mentioned, the term "fatty" compound (for example a fatty acid) denotes for these surfactants a compound comprising, in its main chain, at least one saturated or unsaturated alkyl chain containing at least 6 carbon atoms, preferably from 8 to 30 carbon atoms, and better still from 10 to 22 carbon atoms.

As regards the "anionic surfactants", the term "anionic surfactant" means a surfactant comprising, as ionic or ionizable groups, only anionic groups. These anionic groups are chosen preferably from the groups $CO_2H$, $CO_2^-$, $SO_3H$, $SO_3^-$, $OSO_3H$, $OSO_3^-$, $O_2PO_2H$, $O_2PO_2H^-$ and $O_2PO_2^{2-}$.

The anionic surfactant(s) that may be used in the composition of the invention are especially chosen from alkyl sulfates, alkyl ether sulfates, alkylamido ether sulfates, alkylaryl polyether sulfates, monoglyceride sulfates, alkylsulfonates, alkylamide sulfonates, alkylarylsulfonates, α-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group.

Some of these compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they are not in the form of zinc salts, and they may be chosen from alkali metal salts, such as the sodium or potassium salt, and preferably the sodium salt, ammonium salts, amine salts, and in particular amino alcohol salts, and alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Use is preferably made of ($C_6$-$C_{24}$) alkyl sulfates, ($C_6$-$C_{24}$)alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. More preferentially, the anionic surfactant(s) are chosen from ($C_{10}$-$C_{20}$)alkyl ether sulfates, and in particular sodium lauryl ether sulfate containing 2.2 mol of ethylene oxide.

The term "cationic surfactant" means a surfactant that is positively charged when it is contained in the composition according to the invention. This surfactant may bear one or more positive permanent charges or may contain one or more functions that are cationizable in the composition according to the invention.

The cationic surfactant(s) are preferably selected from primary, secondary or tertiary fatty amines, optionally polyoxyalkylenated, or salts thereof, and quaternary ammonium salts, and mixtures thereof.

The fatty amines generally comprise at least one $C_8$-$C_{30}$ hydrocarbon-based chain. Among the fatty amines that may be used according to the invention, examples that may be mentioned include stearylamidopropyldimethylamine and distearylamine.

Examples of quaternary ammonium salts that may especially be mentioned include:

those corresponding to the general formula (XIV) below

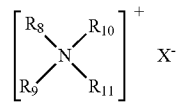

(XIV)

in which the groups $R_8$ to $R_{11}$, which may be identical or different, represent a linear or branched aliphatic group containing from 1 to 30 carbon atoms, or an aromatic group such as aryl or alkylaryl, at least one of the groups $R_8$ to $R_{11}$ denoting a group containing from 8 to 30 carbon atoms, preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (XIV), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, palmitylamidopropyltrimethylammonium salts, stearamidopropyltrimethylammonium salts and stearamidopropyldimethylcetearylammonium salts. It is particularly preferred to use the chloride salts of these compounds.

quaternary ammonium salts of imidazoline, for instance those of formula (XV) below:

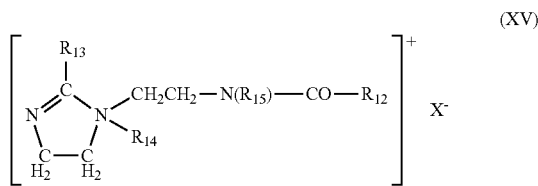

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylarylsulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name Rewoquat® W 75 by the company Rewo;

quaternary diammonium or triammonium salts, in particular of formula (XVI):

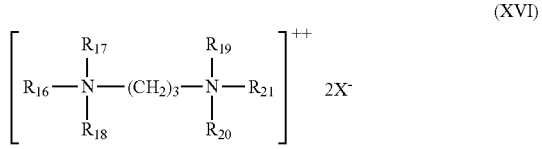

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group ($R_{16a}$)($R_{17a}$)($R_{18a}$)N—(CH$_2$)$_3$;

$R_{16a}$, $R_{17a}$, $R_{18a}$, $R_{18}$, $R_{19}$, $R_{20}$ and $R_{21}$, which may be identical or different, are chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), quaternary ammonium salts containing at least one ester function, such as those of formula (XVII) below:

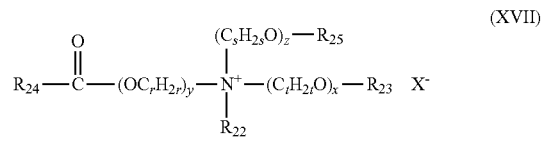

in which:

$R_{22}$ is chosen from $C_1$-$C_6$ alkyl groups and $C_1$-$C_6$ hydroxyalkyl or dihydroxyalkyl groups;

$R_{23}$ is chosen from:

the group

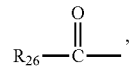

groups $R_{27}$, which are linear or branched, saturated or unsaturated $C_1$-$C_{22}$ hydrocarbon-based groups, a hydrogen atom, $R_{25}$ is chosen from:

the group

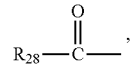

groups $R_{29}$, which are linear or branched, saturated or unsaturated $C_1$-$C_6$ hydrocarbon-based groups, a hydrogen atom, $R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6;

y is an integer ranging from 1 to 10;

x and z, which may be identical or different, are integers ranging from 0 to 10;

X– is a simple or complex, organic or mineral anion;

with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{32}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x y z is from 1 to 10.

When $R_{23}$ is a hydrocarbon-based group $R_{27}$, it may be long and contain from 12 to 22 carbon atoms, or may be short and contain from 1 to 3 carbon atoms.

When $R_{25}$ is an $R_{29}$ hydrocarbon-based group, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion compatible with the ammonium containing an ester function.

The anion $X^-$ is even more particularly chloride or methyl sulfate.

Use is made more particularly, in the composition according to the invention, of the ammonium salts of formula (XVII) in which:

$R_{22}$ denotes a methyl or ethyl group,
x and y are equal to 1;
z is equal to 0 or 1;
r, s and t are equal to 2;
$R_{23}$ is chosen from:
the group

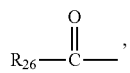

methyl, ethyl or $C_{14}$-$C_{22}$ hydrocarbon-based groups,
a hydrogen atom;
$R_{25}$ is chosen from:
the group

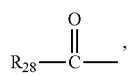

a hydrogen atom;

$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

The hydrocarbon-based groups are advantageously linear.

Mention may be made, for example, of the compounds of formula (XVII) such as the diacyloxyethldimethylammonium, diacyloxyethythydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by quaternization using an alkylating agent such as an alkyl (preferably methyl or ethyl) halide, a dialkyl (preferably methyl or ethyl) sulfate, methyl methanesulfonate, methyl para-toluenesulfonate, glycol chlorohydrin or glycerol chlorohydrin.

Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in U.S. Pat. Nos. 4,874,554 and 4,137,180.

Use may be made of behenoythydroxypropyltrimethylammonium chloride, provided by Kao under the name Quatarmin BTC 131.

Preferably, the ammonium salts containing at least one ester function contain two ester functions.

Among the quaternary ammonium salts containing at least one ester function, which may be used according to the invention, it is preferred to use dipalmitoylethythydroxyethylmethytammonium salts.

The amphoteric or zwitterionic surfactant(s) that may be used in the present invention may especially be secondary or tertiary aliphatic amine derivatives, optionally quaternized, in which the aliphatic group is a linear or branched chain containing from 8 to 22 carbon atoms, the said amine derivatives containing at least one anionic group, for instance a carboxylate, sulfonate, sulfate, phosphate or phosphonate group. Mention may be made in particular of ($C_8$-$C_{20}$)alkylbetaines, sulfobetaines, ($C_8$-$C_{20}$alkyl)amido($C_3$-$C_8$alkyl)betaines or ($C_8$-$C_{20}$alkyl)amido($C_6$-$C_8$alkyl)sulfobetaines.

Among the secondary or tertiary aliphatic amine derivatives, optionally quaternized, that may be used, as defined above, mention may also be made of the compounds of respective structures (B1) and (B2) below:

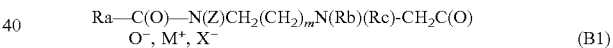

in which formula (B1):

Ra represents a $C_{10}$-$C_{30}$ alkyl or alkenyl group derived from an acid RaCOOH preferably present in hydrolysed coconut oil, or a heptyl, nonyl or undecyl group;

Rb represents a beta-hydroxyethyl group; and

Rc represents a carboxymethyl group;

$M^+$ represents a cationic counterion derived from an alkali metal or alkaline-earth metal, such as sodium, an ammonium ion or an ion derived from an organic amine; and $X^-$ represents an organic or mineral anionic counterion, preferably chosen from halides, acetates, phosphates, nitrates, ($C_1$-$C_4$)alkyl sulfates, ($C_1$-$C_4$)alkyl or ($C_1$-$C_4$)alkylaryl sulfonates, in particular methyl sulfate and ethyl sulfate;

m is equal to 0, 1 or 2;

Z represents a hydrogen atom or a hydroxyethyl or carboxymethyl group;

or alternative $M^+$ and $X^-$ are absent;

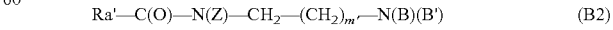

in which formula:

B represents the group —$CH_2$—$CH_2$—O—X';

B' represents the group —$(CH_2)_z$Y', with z=1 or 2;

X' represents the group —$CH_2$—C(O)OH, —$CH_2$—C(O)OZ', —$CH_2$—$CH_2$—C(O)OH, —$CH_2$—$CH_2$—C(O)OZ', or a hydrogen atom;

Y' represents the group —C(O)OH, —C(O)OZ', —CH$_2$—CH(OH)—SO$_3$H or the group —CH$_2$—CH(OH)—SO$_3$—Z';

Z' represents a cationic counterion derived from an alkali metal or alkaline-earth metal, such as sodium, an ammonium ion or an ion derived from an organic amine;

Ra' represents a C$_{10}$-C$_{30}$ alkyl or C$_{10}$-C$_{30}$ alkenyl group of an acid Ra'—COOH, which is preferably present in coconut oil or in hydrolysed linseed oil, or an alkyl group, especially a C$_{17}$ alkyl group and its iso form, or an unsaturated C$_{17}$ group, m' is equal to 0, 1 or 2, Z represents a hydrogen atom or a hydroxyethyl or carboxymethyl group.

The compounds of this type are classified in the CTFA dictionary, 5th edition, 1993, under the names disodium cocoamphodiacetate, disodium lauroamphodiacetate, disodium caprylamphodiacetate, disodium caryloamphodiacetate, disodium cocoamphodipropionate, disodium lauroamphodipropionate, disodium caprylamphodipropionate, disodium capryloamphodipropionate, lauroamphodipropionic acid, cocoamphodipropionic acid and hydroxyethylcarboxymethylcocamidopropylamine.

Examples that may be mentioned include the cocoamphodiacetate sold by the company Rhodia under the trade name Miranol® C2M Concentrate or under the trade name Miranol Ultra. C 32 and the product sold by the company Chimex under the trade name Chimexane HA.

Use may also be made of compounds of formula (B'2):

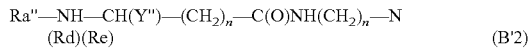

in which formula:

Y" represents the group —C(O)OH, —C(O)OZ", —CH$_2$—CH (OH)—SO$_3$H or the group CH$_2$—CH(OH)—SO$_3$—Z";

Rd and Re, independently of each other, represent a C$_1$-C$_4$ alkyl or hydroxyalkyl radical;

Z" represents a cationic counterion derived from an alkali metal or alkaline-earth metal, such as sodium, an ammonium ion or an ion derived from an organic amine;

Ra" represents a C$_{10}$-C$_{30}$ alkyl or alkenyl group of an acid Ra'"—C(O)OH which is preferably present in coconut oil or in hydrolysed linseed oil;

n and n' denote, independently of each other, an integer ranging from 1 to 3.

Among the compounds of formula (B'2), mention may be made of the compound classified in the CTFA dictionary under the name sodium diethylaminopropyl cocoaspartamide and sold by the company Chimex under the name Chimexane HB.

Among the abovementioned amphoteric or zwitterionic surfactants, it is preferred to use (C$_8$-C$_{20}$ alkyl)betaines such as cocoylbetaine, (C$_8$-C$_{20}$ alkyl)amido(C$_2$-C$_8$ alkyl)betaines such as cocoylamidopropylbetaine, and mixtures thereof.

More preferentially, the amphoteric or zwitterionic surfactant(s) are chosen from cocoylamidopropylbetaine and cocoylbetaine.

The surfactants used in the composition according to the invention are preferably nonionic or cationic.

The surfactant(s) may be present in an amount ranging from 0.01% to 30% by weight, preferably from 0.1% to 10% by weight and better still from 1% to 5% by weight relative to the total weight of the composition.

The composition according to the invention advantageously comprises water, which advantageously represents from 1% to 95%, preferably from 20% to 80% and better still from 40% to 70% by weight relative to the total weight of the composition.

The composition according to the invention may also comprise one or more fatty substances.

The term "fatty substance" means an organic compound that is insoluble in water at ordinary room temperature (25° C.) and at atmospheric pressure (760 mmHg), with a solubility in water of less than 5%, preferably less than 1% and even more preferentially less than 0.1%.

In addition, the fatty substances are generally soluble in organic solvents under the same temperature and pressure conditions, for instance chloroform, ethanol, benzene, liquid petroleum jelly or decamethylcyclopentasiloxane.

The said fatty substance(s) that may be used in the composition according to the invention are preferably chosen from hydrocarbons, fatty alcohols, fatty acid and/or fatty alcohol esters, non-salified fatty acids, silicones and mixtures thereof.

The fatty substance(s) may be liquid or non-liquid at room temperature and at atmospheric pressure.

The said fatty substance(s) may represent from 0.001% to 90% by weight, better still from 0.1% to 50% by weight, preferably from 0.5% to 30% by weight and better still from 1% to 20% by weight, relative to the total weight of the composition.

The composition may also comprise one or more water-soluble organic solvents (solubility of greater than or equal to 5% in water at 25° C. and at atmospheric pressure).

Examples of water-soluble organic solvents that may be mentioned include linear or branched and preferably saturated monoalcohols or diols, comprising 2 to 10 carbon atoms, such as ethyl alcohol, isopropyl alcohol, hexylene glycol (2-methyl-2,4-pentanediol), neopentyl glycol and 3-methyl-1,5-pentanediol, butylene glycol, dipropylene glycol and propylene glycol; aromatic alcohols such as phenylethyl alcohol; polyols containing more than two hydroxyl functions, such as glycerol; polyol ethers, for instance ethylene glycol monomethyl, monoethyl and monobutyl ethers, propylene glycol or ethers thereof, for instance propylene glycol monomethyl ether; and also diethylene glycol alkyl ethers, especially C$_1$-C$_4$ alkyl ethers, for instance diethylene glycol monoethyl ether or monobutyl ether, alone or as a mixture.

The water-soluble organic solvents, when they are present, generally represent between 1% and 20% by weight relative to the total weight of the composition according to the invention, and preferably between 5% and 10% by weight relative to the total weight of the composition.

The composition according to the invention may also contain one or more additives chosen from the active principles and cosmetic adjuvants commonly used in the field of haircare. These additives are chosen, for example, from fixing polymers other than the thickening polymers already mentioned, conditioning agents and especially cationic polymers, silicones, chitosans and derivatives, hydrophobic solvents, hair dyes such as direct dyes, in particular cationic or natural dyes, oxidation dyes and pigments; UV-screening agents, fillers such as nacres, titanium dioxide, resins and clays; fragrances, peptizers, vitamins, preserving agents, acidic agents, alkaline agents, reducing agents, oxidizing agents, amino acids, oligopeptides, peptides, hydrolysed or non-hydrolysed, modified or unmodified proteins, enzymes, organic acids, antioxidants and free-radical scavengers, chelating agents, antidandruff agents, seborrhoea regulators, calmatives, plasticizers, glitter flakes and propellent gases.

The above additives may be present in an amount ranging from 0.01% to 20% by weight relative to the total weight of the composition according to the invention.

The composition according to the invention may be in the form of a wax, a paste, a cream, a gel, a foam, a spray or a lotion.

A subject of the present invention is also the use of the composition as defined according to the invention for straightening keratin fibres, preferably the hair.

Finally, a subject of the invention is also a process for straightening keratin fibres, preferably the hair, comprising:

(i) a step of applying to the keratin fibres the composition according to the invention, followed by;

(ii) a step of raising the temperature of the keratin fibres via a heating means, to a temperature ranging from 25 to 250° C.

Preferably, the temperature is raised by means of the said heating means to a temperature ranging from 100 to 250° C. and better still from 150 to 230° C.

In a first embodiment, the composition according to the invention is applied to a wet or dry head of hair, preferably wet hair, with or without a leave-on time. The bath ratio of the applied formulation may range from 0.1 to 10 and more particularly from 0.2 to 5. The keratin fibres are then optionally rubbed dry, preferably rubbed dry. One or more heating means are applied once or in succession to the keratin fibres at a temperature ranging from 25 to 250° C., preferably from 100 to 250° C. and better still from 150 to 230° C. for a time ranging from 5 seconds to 1 hour and preferably from 5 seconds to 1 minute. The hair then optionally undergoes one or more of the following operations: rinsing, shampooing and treatment with a rinse-out hair conditioner, drying, preferably using a hood or a hairdryer.

Preferably, when a leave-on time is observed, the said leave-on time is preferably from 5 minutes to 1 hour.

The term "bath ratio" means the ratio between the total weight of the applied composition and the total weight of keratin fibres to be treated.

Heating means that may especially be used include a straightening iron, a curling iron, a crimping iron, a waving iron, a hood, a hairdryer, an infrared heating system or a heating roller (of the digital perm type).

In a second embodiment, the sequence formed by the steps: (i) application of the composition according to the invention to keratin fibres, followed by (ii) raising the temperature of the keratin fibres, via a heating means, to a temperature ranging from 25 to 250° C., is performed one or more times, optionally separated by one or more cosmetic treatments, preferably shampooing, until the desired shape or shape intensity is obtained.

In these two embodiments, the heating means is preferably an iron.

The examples that follow serve to illustrate the invention without, however, being limiting in nature.

EXAMPLE 1

Compositions 1 to 2 for straightening keratin fibres according to the invention are prepared, along with a control composition not containing any thickener according to the invention. The formulations are indicated in Table I (the amounts are expressed as weight percentages relative to the total weight of the composition).

TABLE I

| Composition | Compound | Weight % of active material |
| --- | --- | --- |
| Control | Urea | 10% |
|  | Water | qs 100% |
| 1 | Urea | 10% |
|  | Cetyhydroxyethylcelluose[a] | 1% |
|  | Water | qs 100% |
| 2 | Urea | 10% |
|  | SMDI/polyethylene glycol polymer bearing decyl end groups, as a water-glycol solution[b] | 8.5% |
|  | Water | qs 100% |

(a) The cetylhydroxyethylcellulose used is sold under the name Polysurf 67CS by the company Ashland.

(b) the SMDI/polyethylene glycol polymer bearing decyl end groups, as a water-glycol solution, used is sold under the name Aculyn 44 by the company Röhm & Haas.

Compositions 1 and 2 and the control composition are applied to locks of moderately curly hair (curliness level 3 according to the article *Shape variability and classification of human hair*, Roland De La Mettrie et al., Human Biology, 2007, vol. 79, No. 3, pages 265-281) according to the following protocol:

The keratin fibres are prewashed with a shampoo.

Each composition is applied to a separate wet lock. The excess product is then removed by rubbing dry.

The locks are then predried with a hairdryer. A straightening iron is then applied slowly along the locks twice in succession at a temperature of 210° C. (for about 1 minute). The locks are then shampooed and are finally dried using a hairdryer.

The Applicant finds that the straightening of the hair for the two compositions according to the invention and the control composition is persistent.

On the other hand, the Applicant finds that the working qualities in terms of ease of distribution onto the head of hair, the ease of blow-drying and the ease of passage of flat tongs are greater in the case of compositions 1 and 2 according to the invention relative to the control composition.

Furthermore, the Applicant finds that compositions 1 and 2 according to the invention afford the hair greater sheen and cosmeticity than the control composition.

EXAMPLE 2

Composition 3 for straightening keratin fibres according to the invention is prepared, along with a control composition not containing any thickener according to the invention. The formulations are indicated in Table II (the amounts are expressed as weight percentages relative to the total weight of the composition).

TABLE II

| Composition | Compound | Weight % of active material |
| --- | --- | --- |
| Control | Urea | 5% |
|  | Water | qs 100% |
| 3 | Urea | 5% |
|  | Crosslinked acrylic acid/alkyl acrylate polymer[a] | 1% |
|  | Water | qs 100% |

(a) The crosslinked acrylic acid; alkyl acrylate polymer used is sold under the name Pemulen TR-2 Polymer by the company Lubrizol.

Composition 3 and the control composition are applied to locks of moderately curly hair (curliness level 3 according to the article *Shape variability and classification of human hair*, Roland De La Mettrie et al., Human Biology, 2007, vol. 79, No. 3, pages 265-281) according to the following protocol:

The keratin fibres are prewashed with a shampoo.

Each composition is applied to a separate wet lock. The excess product is then removed by rubbing dry.

The locks are then predried with a hairdryer. A straightening iron is then applied slowly along the locks twice in succession at a temperature of 210° C. (for about 1 minute). The locks are then shampooed and are finally dried using a hairdryer. The Applicant finds that the straightening of the hair for composition 3 according to the invention and the control composition is persistent.

On the other hand, the Applicant finds that the working qualities in terms of ease of distribution onto the head of hair, the ease of blow-drying and the ease of passage of flat tongs are greater in the case of composition 3 according to the invention relative to the control composition.

Furthermore, the Applicant finds that composition 3 according to the invention affords the hair greater sheen and cosmeticity than the control composition.

The invention claimed is:

1. A process for straightening hair, comprising:
   (i) applying to the hair a composition comprising:
      (a) urea, present in an amount ranging from 2% to 12% by weight, relative to the total weight of the composition; and
      (b) cetyl hydroxyethylcellulose, present in an amount ranging from 0.2% to 10% by weight, relative to the total weight of the composition; and
   (ii) raising the temperature of the hair via a heating tool, to a temperature ranging from about 100 to about 250° C.

2. The process according to claim 1, wherein the urea is present in an amount ranging from about 2% to about 10% by weight, relative to the total weight of the composition.

3. The process according to claim 1, wherein the cetyl hydroxyethylcellulose is water-soluble or water-dispersible at a pH of 7 and at room temperature (25° C.).

4. The process according to claim 1, wherein the heating tool is an iron.

5. The process according to claim 1, wherein the composition further comprises water.

6. The process according to claim 1, wherein the composition further comprises water in an amount ranging from 1% to 95% by weight, relative to the total weight of the composition.

7. The process according to claim 1, wherein the composition further comprises water in an amount ranging from 20% to 80% by weight, relative to the total weight of the composition.

8. The process according to claim 1, wherein the composition further comprises water in an amount ranging from 40% to 70% by weight, relative to the total weight of the composition.

9. The process according to claim 1, wherein the hair is wet when the composition is applied thereto.

10. The process according to claim 9, wherein the hair is dried after the composition is applied thereto and before the temperature of the hair is raised.

11. The process according to claim 1, wherein the composition is applied to the hair in a bath ratio ranging from 0.1 to 10.

* * * * *